United States Patent
Gelmi et al.

(10) Patent No.: US 9,308,184 B2
(45) Date of Patent: Apr. 12, 2016

(54) POWDER COMPOSITION FOR DISINFECTION OF THE TEATS OF DAIRY ANIMALS

(71) Applicant: I.C.F. S.R.L., Palazzo Pignano (IT)

(72) Inventors: Fabio Gelmi, Cremona (IT); Maurizio Venturini, Cremona (IT)

(73) Assignee: I.C.F. S.R.L., Palazzo Pignano (IT)

( * ) Notice: Subject to any disclaimer, the term of this patent is extended or adjusted under 35 U.S.C. 154(b) by 0 days.

(21) Appl. No.: 14/438,904

(22) PCT Filed: Nov. 6, 2013

(86) PCT No.: PCT/EP2013/073113
§ 371 (c)(1),
(2) Date: Apr. 28, 2015

(87) PCT Pub. No.: WO2014/072315
PCT Pub. Date: May 15, 2014

(65) Prior Publication Data
US 2015/0297542 A1      Oct. 22, 2015

(30) Foreign Application Priority Data

Nov. 7, 2012  (EP) .................... 12191564

(51) Int. Cl.
| | |
|---|---|
| *A61K 31/18* | (2006.01) |
| *A61K 47/10* | (2006.01) |
| *A61K 47/36* | (2006.01) |
| *A61K 9/14* | (2006.01) |
| *A61K 9/00* | (2006.01) |
| *A61K 9/06* | (2006.01) |
| *A61K 45/06* | (2006.01) |
| *A61K 31/723* | (2006.01) |
| *A61K 31/715* | (2006.01) |
| *A61K 31/047* | (2006.01) |
| *A01N 59/00* | (2006.01) |
| *A01N 41/06* | (2006.01) |

(52) U.S. Cl.
CPC ................ *A61K 31/18* (2013.01); *A01N 41/06* (2013.01); *A01N 59/00* (2013.01); *A61K 9/0017* (2013.01); *A61K 9/06* (2013.01); *A61K 9/145* (2013.01); *A61K 9/148* (2013.01); *A61K 31/047* (2013.01); *A61K 31/715* (2013.01); *A61K 31/723* (2013.01); *A61K 45/06* (2013.01); *A61K 47/10* (2013.01); *A61K 47/36* (2013.01)

(58) Field of Classification Search
None
See application file for complete search history.

(56) References Cited

U.S. PATENT DOCUMENTS

| | | | | |
|---|---|---|---|---|
| 5,635,492 | A | * | 6/1997 | Corby .................. A61K 9/0041 424/670 |
| 6,559,199 | B1 |   | 5/2003 | Pusineri et al. |
| 7,371,398 | B2 | * | 5/2008 | Schneider ................ A01J 7/04 424/405 |
| 2004/0225017 | A1 |   | 11/2004 | Schneider |

FOREIGN PATENT DOCUMENTS

| | | |
|---|---|---|
| DE | 10236096 A1 | 2/2004 |
| EP | 0904693 A1 | 3/1999 |
| EP | 1932425 A2 | 6/2008 |

OTHER PUBLICATIONS

International Search Report PCT/EP2013/073113 Jan. 31, 2014.

* cited by examiner

*Primary Examiner* — Brian J Davis
(74) *Attorney, Agent, or Firm* — King & Schickli, PLLC

(57) ABSTRACT

A powder composition for the post-milking teat disinfection of dairy animals is described. In particular, said composition has proven to be advantageously effective as bactericidal agent, while without causing irritation or reddening of the skin.

17 Claims, No Drawings

POWDER COMPOSITION FOR DISINFECTION OF THE TEATS OF DAIRY ANIMALS

FIELD OF THE INVENTION

The present invention relates to a powder composition for the post-milking teat disinfection of dairy animals.

BACKGROUND OF THE INVENTION

Products having a disinfectant action to protect the mammary system in dairy animals from contamination by microorganisms such as bacteria and fungi that are the cause of recurring infections are known.

The disinfectants currently used for this purpose are in fluid state and are in the form of more or less viscous liquids.

These disinfectants, as being marketed in liquid form and packaged in large containers, require large spaces for storage before use.

Furthermore, organic chlorine-based products are known, also used in preparations intended for human use, such as skin disinfectants. In the veterinary field, the use of known organic chlorine-based compositions for the post-milking teat disinfection of dairy animals presents several drawbacks that can be primarily ascribable to the high dosages that must be used to obtain significant advantageous effects.

A first drawback attributable to the use of organic chlorine compounds at high dosage is associated, for example, to the irritant and inflammatory effect to the skin of the animals; in addition, if inhaled, it is an irritant to the respiratory tracts thereof. The onset of said side effects may require that treatment be discontinued before the desired results have been achieved.

A second drawback ascribable to the use of known organic chlorine-based compositions is associated to the fact that a high dosage thereof can also result in irritant and inflammatory effects to the operator during use of the product.

The object of the present invention is to find a product that is effective for the aforementioned applications, but which at the same time allows the drawbacks reported for the treatments of the prior art to be overcome.

SUMMARY OF THE INVENTION

The above object has been achieved by a powder composition comprising sorbitol, chloramine-T and natural gum, wherein the sorbitol and chloramine-T are in a weight ratio of at least 3:1.

In another aspect the present invention concerns the use of said composition for the post-milking teat disinfection of dairy animals.

The characteristics and advantages of the present invention will be evident from the detailed description given below, and from the illustrative non-limiting working examples.

DETAILED DESCRIPTION OF THE INVENTION

The subject of the invention is therefore a powder composition comprising sorbitol, chloramine-T and natural gum, wherein the sorbitol and chloramine-T are in a weight ratio of at least 3:1.

It has been surprisingly found that said powder composition is capable of effectively disinfecting the teats of dairy animals after milking, advantageously allowing the use of low doses of chloramine-T, while at the same time ensuring a prolonged emollient effect over time. In addition, since prior to use said composition is dissolved in an aqueous means, the natural gum in powder form generates a colloidal, high-viscosity dispersion that is capable of adhering to the teats of the animals, so as to prolong the contact times of the composition with the areas to be disinfected.

In addition, a further advantage of the use of a powder composition is the high stability of the chloramine-T compared to the stability of the chlorinated compounds in aqueous solution. This means that the storage times of said composition are extremely and significantly increased, not only in respect of the corresponding aqueous solutions, but also in respect of the known products.

It was therefore surprisingly found that by combining sorbitol and chloramine-T in suitable weight ratios, it is possible to obtain a powder composition for veterinary use having a high emollient and, at the same time, disinfectant efficacy advantageously at low chlorine doses.

Preferably, in said powder composition, the sorbitol and chloramine-T are in a weight ratio of 3.5:1 to 7:1.

More preferably, the sorbitol and chloramine-T are in a weight ratio of 4:1 to 6:1. According to a preferred embodiment, the sorbitol and chloramine-T are in a weight ratio of 4.4:1.

Preferably, the powder composition comprises sorbitol, chloramine-T and natural gum, wherein the sorbitol and natural gum are in a weight ratio of at least 1.4:1.

Preferably, in said powder composition, the sorbitol and natural gum are in a weight ratio of 1.6:1 to 5:1.

More preferably, the sorbitol and natural gum are in a weight ratio of 1.8:1 to 3:1.

According to a preferred embodiment, the sorbitol and natural gum are in a weight ratio of about 2.02:1.

Said natural gum is preferably selected from the group consisting of gum arabic, tragacanth, guar gum, xanthan gum and mixtures thereof.

According to a preferred embodiment, said natural gum is xanthan gum.

It has been surprisingly found that the presence of natural gum generates a gel, after dissolution of the powder in water. The gel consistency of the composition of the invention increases the contact times, thus enhancing the action of chloramine-T, consequently allowing the use of this compound, efficacy of treatment being equal, in advantageously and significantly lower quantities than the concentrations known in the prior art. In addition, the composition of the invention does not require surfactants of any type and this is a further advantage, not only from an ecological point of view, but also from the point of view of skin tolerance, since surfactants can be irritant and desiccant.

Preferably, the above described composition comprises 50-70 wt % sorbitol, 20-40 wt % natural gum and 10-15 wt % chloramine-T, based on the weight of the composition.

More preferably, the composition comprises 55-65 wt % sorbitol, 25-35 wt % natural gum and 12-14 wt % chloramine-T.

The composition of the invention can also comprise an anti-caking agent selected from the group consisting of silicon dioxide, tricalcium phosphate, hydrophobic starch derivatives, cellulose powder, calcium silicate, magnesium silicate, aluminium silicate, sodium silicate, sodium bicarbonate, sodium ferrocyanide, potassium ferrocyanide calcium ferrocyanide, magnesium trisilicate, talc, sodium aluminosilicate, potassium aluminosilicate, calcium aluminosilicate, bentonite, stearic acid, polydimethylsiloxane, polyacrylic acid and respective sodium salts, sodium polyalkyl naphthalene sulphonate and mixtures thereof.

According to a preferred embodiment, the anti-caking agent is silicon dioxide.

Said anti-caking agent is preferably present in an amount of 0.1-3 wt %, based on the weight of the composition, more preferably 0.3-1 wt %.

Preferably, the powder composition further comprises a powder dye. Indeed, advantageously, following the solubilisation of the composition in an aqueous means prior to use, said dye gives the composition an intense colour thus allowing the treated areas to be traced. More preferably, once in water, said dye presents an intense blue colour. In the composition of the invention, the dye is present in an amount of 0.01-10 wt %, on to the total weight of the composition, preferably 0.1-5 wt %, more preferably 0.5-3 wt %.

According to a preferred embodiment, the powder composition consists essentially of sorbitol, chloramine-T and natural gum, wherein the sorbitol and chloramine-T are in a weight ratio of at least 3:1, wherein the term "consists essentially of" means that sorbitol, chloramine-T and natural gum are the only ingredients having disinfecting and emollient properties, and that no surfactants are present. It should be understood that the aspects above indicated as being advantageous and preferred for the composition of the invention are to be considered analogously advantageous and preferred for this preferred embodiment.

According to another preferred embodiment, the powder composition of the invention consists of sorbitol, chloramine-T, natural gum, a dye, an anti-caking agent, wherein the sorbitol and chloramine-T are in a weight ratio of at least 3:1. It should be understood that the aspects above indicated as being advantageous and preferred for the composition of the invention are to be considered analogously advantageous and preferred also for this preferred embodiment.

According to a particularly preferred embodiment, the powder composition of the invention comprises:
50-70 wt % sorbitol,
20-40 wt % natural gum,
10-15 wt % chloramine-T,
0.1-3 wt % anti-caking agent, and
0.01-10 wt % dye.

In another aspect, the invention concerns a unit dose of the above-described powder composition comprising:
50-70 g of sorbitol,
20-40 g of natural gum,
10-15 g of chloramine-T,
0.1-3 g of anti-caking agent, and
0.01-10 g of dye.
Preferably, said unit dose consists of:
55-65 g of sorbitol,
25-35 g of natural gum,
12-14 g of chloramine-T,
0.3-1 g of anti-caking agent, and
0.5-3 g of dye.

According to a preferred embodiment, said unit dose comprises 100 g of the powder composition of the invention.

The composition and the unit dose of the present invention are prepared by mixing the powder compounds in the weight ratio as defined above.

In a further aspect, the invention relates to the use of the powder composition of the invention in the veterinary field, since it allowed significantly satisfactory results to be achieved in the post-milking disinfection of dairy animal teats, having shown an optimal bactericidal effect, without causing any skin irritation.

The powder composition of the invention therefore finds advantageous and convenient application as anti-inflammatory and antibacterial agent in the treatment for the prevention of animal conditions such as ulcerations and mastitis.

In such uses, said composition or said unit dose are preliminarily dispersed in an aqueous medium, preferably water, to form a gel, prior to application. More preferably, said composition or said unit dose are dispersed in a concentration of 10-30 g/l, more preferably 15-25 g/l, in water; after about at least 1 hour, preferably after 2-3 hours, the resulting gel mixture can be applied to the teats of the animals after milking, for example by dipping.

Alternatively, the composition of the invention or the unit dose are used as a bactericide in the treatment of surfaces or supports.

It is to be understood that all aspects identified as preferred and advantageous for the composition of the invention, are to be deemed analogously preferred and advantageous also for the unit dose, and both the medical and non-medical uses of said composition.

Working examples of the present invention provided for illustrative purposes are reported herein below.

Example 1

100 g or a composition for veterinary use in powder form were prepared in accordance with the present invention, by mixing:
57.2 g of sorbitol,
28.3 g of natural gum,
13 g of chloramine-T,
0.5 g of silicon dioxide, and
1 g of dye.

The composition was dispersed in 5 liters of water and allowed to stand for 2 hours.

The resulting gel mixture was then used in the post-milking disinfection treatment of the teats of 100 cows. No redness or irritation following application was observed, thus demonstrating that the composition of the invention is perfectly tolerated by the skin.

In addition, the cows periodically treated with the same composition did not develop either local ulceration or mastitis over time, thus demonstrating that the composition of the invention also allows an effective prevention action against these conditions.

Example 2

100 g or a composition for veterinary use in powder form were prepared in accordance with the present invention, by mixing:
65 g of sorbitol,
23 g of natural gum,
10 g of chloramine-T,
1 g of sodium silicate, and
1 g of dye.

The composition was dispersed in 5 liters of water and allowed to stand for 3 hours.

The resulting gel mixture was then used in the post-milking disinfection treatment of the teats of 100 goats. No redness or irritation following application was observed, demonstrating that the composition of the invention is perfectly tolerated by the skin.

In addition, the goats periodically treated with the same composition did not develop either local ulceration or mastitis over time, thus demonstrating that the composition of the invention also allows an effective prevention action against these conditions.

Example 3

100 g or a composition for veterinary use in powder form were prepared in accordance with the present invention, by mixing:

55 g of sorbitol,
28 g of natural gum,
16 g of chloramine-T,
0.5 g of calcium silicate, and
0.5 g of dye.

The composition was dispersed in 5 liters of water and allowed to stand for 2.5 hours.

The resulting gel mixture was then used in the post-milking disinfection treatment of the teats of 100 sheep. No redness or irritation following application was observed, demonstrating that the composition of the invention is perfectly tolerated by the skin.

In addition, the sheep periodically treated with the same composition did not develop either local ulceration or mastitis over time, thus demonstrating that the composition of the invention also allows an effective prevention action against these conditions.

Example 4

Evaluation of the Bactericidal Action of the Composition of the Invention

The composition of Example 1 was tested to check its bactericidal action.

In particular, in accordance with the European Standard EN 1656:2009, the bactericidal action of the composition on the following bacterial strains was evaluated:

*Staphylococcus aureus* ATCC6538,
*Streptococcus uberis* ATCC19436,
*Escherichia coli* ATCC10536.

The composition was tested at the following concentrations: 80% (maximum testable concentration), 50%, and 25%.

The contact time was 5 minutes at a temperature of 30° C.±1° C.

The interfering substance was skimmed milk with a final concentration of 1%.

The results of said tests are recorded in Tables 1-3 below.

TABLE 1

| Microorganism test | Dil | N cfu/plate | N cfu/plate | Nv cfu/plate | Nv cfu/plate |
|---|---|---|---|---|---|
| *Staphylococcus aureus* ATCC6538 | −6 | >330 | >330 | 86 | 102 |
| | −7 | 38 | 42 | | |
| | | 8.60 | VALID | 9.4E+02 | |
| *Streptococcus uberis* ATCC19436 | −6 | >330 | >330 | 94 | 80 |
| | −7 | 50 | 46 | | |
| | | 8.68 | VALID | 8.7E+02 | |
| *Escherichia coli* ATCC10536 | −6 | >330 | >330 | 77 | 82 |
| | −7 | 38 | 41 | | |
| | | 8.60 | VALID | 8.0E+02 | |

N: bacterial suspension count cfu/ml
Nv: bacterial suspension count for the preliminary assay cfu/ml

TABLE 2

| Microorganism test | Dil | A cfu/plate | A cfu/plate | B cfu/plate | B cfu/plate | C cfu/plate | C cfu/plate |
|---|---|---|---|---|---|---|---|
| *Staphylococcus aureus* ATCC6538 | −6 | 102 | 108 | 70 | 77 | 83 | 85 |
| | −7 | | 1.1E+02 | | 7.4E+01 | | 8.4E+01 |
| *Streptococcus uberis* ATCC19436 | −6 | 81 | 93 | 77 | 86 | 90 | 92 |
| | −7 | | 8.7E+01 | | 8.2E+01 | | 9.1E+01 |
| *Escherichia coli* ATCC10536 | −6 | 69 | 59 | 70 | 75 | 78 | 74 |
| | −7 | | 6.4E+01 | | 7.3E+01 | | 7.6E+01 |

A: count in experimental conditions validation check cfu/ml
B: count in the neutralizing agent toxicity check cfu/ml
C: count in the neutralizing agent efficacy check cfu/ml

TABLE 3

| Microorganism test | CONCENTRATIONS AND CONTACT TIMES cfu/plate | | | | | |
|---|---|---|---|---|---|---|
| | 80% | 5 min | 50% | 5 min | 25% | 5 min |
| *Staphylococcus aureus* ATCC6538 | 0 Na = <2.15 R = >5.45 | 0 | 0 Na = <2.15 R = >5.45 | 0 | 33 Na = 2.61 R = 4.99 | 48 |
| *Streptococcus uberis* ATCC19436 | 0 Na = <2.15 R = >5.53 | 0 | 0 Na = <2.15 R = >5.53 | 0 | 33 Na = 2.45 R = 5.23 | 24 |
| *Escherichia coli* ATCC10536 | 0 Na = <2.15 R = >5.45 | 0 | 0 Na = <2.15 R = >5.45 | 0 | 80 Na = 2.88 R = 4.72 | 72 |

Na = test mixture count ufc/ml
R = reduced viability

From the data obtained, it resulted that the composition of the invention showed bactericidal activity, advantageously already at a 50% concentration.

The invention claimed is:

1. Powder composition comprising sorbitol, chloramine-T and natural gum, wherein the sorbitol and chloramine-T are in a weight ratio of at least 3:1.

2. The composition of claim 1, wherein the sorbitol and chloramine-T are in a weight ratio of 3.5:1 to 7:1.

3. The composition of claim 2, wherein the sorbitol and chloramine-T are in a weight ratio of 4:1 to 6:1.

4. The composition of claim 1, wherein the sorbitol and natural gum are in a weight ratio of at least 1.4:1.

5. The composition of claim 4, wherein the sorbitol and natural gum are in a weight ratio of 1.6:1 to 5:1.

6. The composition of claim 1, wherein said natural gum is selected from the group consisting of gum arabic, tragacanth, guar gum, xanthan gum and mixtures thereof.

7. The composition of claim 1, comprising 50-70 wt % sorbitol, 20-40 wt % natural gum and 10-15 wt % chloramine-T, based on the weight of the composition.

8. The composition of claim 1, comprising 55-65 wt % sorbitol, 25-35 wt % natural gum and 12-14 wt % chloramine-T, based on the weight of the composition.

9. The composition of claim 1, further comprising an anti-caking agent selected from the group consisting of silicon dioxide, tricalcium phosphate, hydrophobic starch derivatives, cellulose powder, calcium silicate, magnesium silicate, aluminium silicate, sodium silicate, sodium bicarbonate, sodium ferrocyanide, potassium ferrocyanide, calcium ferrocyanide, magnesium trisilicate, talc, sodium aluminosilicate, potassium aluminosilicate, calcium aluminosilicate, bentonite, stearic acid, polydimethylsiloxane, polyacrylic acid and respective sodium salts, sodium polyalkyl naphthalene sulphonate and mixtures thereof.

10. The composition of claim 1, further comprising a powder dye.

11. The composition of claim 1, comprising:
50-70 wt % sorbitol,
20-40 wt % natural gum,
10-15 wt % chloramine-T,
0.1-3 wt % anti-caking agent, and
0.01-10 wt % dye.

12. Unit dose of the composition of claim 1, comprising:
50-70 g of sorbitol,
20-40 g of natural gum,
10-15 g of chloramine-T,
0.1-3 g anti-caking agent, and
0.01-10 g of dye.

13. A method for disinfecting teats of diary animals in a post-milking treatment, said method comprising the application of the composition of claim 1, as a bactericidal agent, to the teats of diary animals.

14. A method for the prevention of teat conditions in dairy animals, said teat conditions being selected from ulcers and mastitis, said method comprising the application of the composition of claim 1 to the teats of dairy animals.

15. A method for disinfecting surfaces or supports, said method comprising the application of the composition of claim 1 or unit dose of claim 12, as a bactericidal agent, to the surfaces or supports.

16. A method for disinfecting teats of diary animals in a post-milking treatment, said method comprising the application of the unit dose of claim 12, as a bactericidal agent, to the teats of diary animals.

17. A method for disinfecting surfaces or supports, said method comprising the application of the unit dose of claim 12, as a bactericidal agent, to the surfaces or supports.

* * * * *